United States Patent
Yun et al.

(10) Patent No.: US 11,858,886 B2
(45) Date of Patent: Jan. 2, 2024

(54) PROCESS OF SELECTIVELY HYDROGENATING GAS MIXTURE HAVING HIGH ACETYLENE CONTENT

(71) Applicant: SK Innovation Co., Ltd., Seoul (KR)

(72) Inventors: Dong Min Yun, Daejeon (KR); Ju Hwan Im, Daejeon (KR); Hee Soo Kim, Daejeon (KR); Do Kyoung Kim, Daejeon (KR); Dae Hyun Choo, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 17/973,975

(22) Filed: Oct. 26, 2022

(65) Prior Publication Data

US 2023/0131732 A1    Apr. 27, 2023

(30) Foreign Application Priority Data

Oct. 27, 2021    (KR) .......................... 10-2021-0144229

(51) Int. Cl.
| | |
|---|---|
| *C07C 5/08* | (2006.01) |
| *B01J 23/89* | (2006.01) |
| *B01J 35/10* | (2006.01) |
| *B01J 37/18* | (2006.01) |
| *B01J 37/02* | (2006.01) |

(52) U.S. Cl.
CPC ............. *C07C 5/08* (2013.01); *B01J 23/8926* (2013.01); *B01J 35/1019* (2013.01); *B01J 35/1042* (2013.01); *B01J 35/1061* (2013.01); *B01J 37/0234* (2013.01); *B01J 37/18* (2013.01); *B01J 2523/17* (2013.01); *B01J 2523/824* (2013.01); *C07C 2523/72* (2013.01); *C07C 2523/89* (2013.01)

(58) Field of Classification Search
CPC ... C07C 5/08; C07C 2523/72; C07C 2523/89; B01J 23/8926; B01J 35/1019; B01J 35/1042; B01J 35/1061; B01J 37/0234; B01J 37/18; B01J 2523/17; B01J 2523/824
See application file for complete search history.

(56) References Cited

U.S. PATENT DOCUMENTS

| | | | | |
|---|---|---|---|---|
| 2004/0024272 A1* | 2/2004 | Cheung | .................... | B01J 23/50 502/224 |
| 2009/0326288 A1* | 12/2009 | Mamadov | ................ | B01J 23/44 585/273 |

FOREIGN PATENT DOCUMENTS

KR    1020180113448 A    10/2018

* cited by examiner

*Primary Examiner* — Thuan D Dang
(74) *Attorney, Agent, or Firm* — THE WEBB LAW FIRM

(57) ABSTRACT

Disclosed is a process for converting methane into value-added compounds. In this process, a gas mixture containing hydrogen as well as high-concentration acetylene formed through methane pyrolysis (e.g. non-oxidative coupling of methane) is selectively hydrogenated in the presence of a bimetallic supported catalyst. This process obtains ethylene from acetylene in the gas mixture while unreacted methane and hydrogen are recovered as byproducts and/or additionally recycled.

16 Claims, 8 Drawing Sheets

Fig. 8A
Fig. 8B
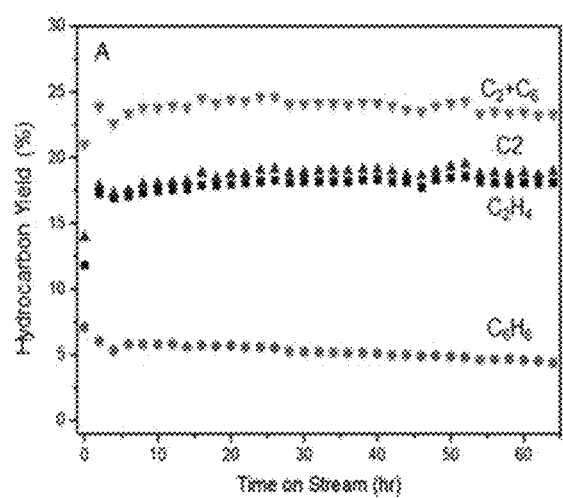
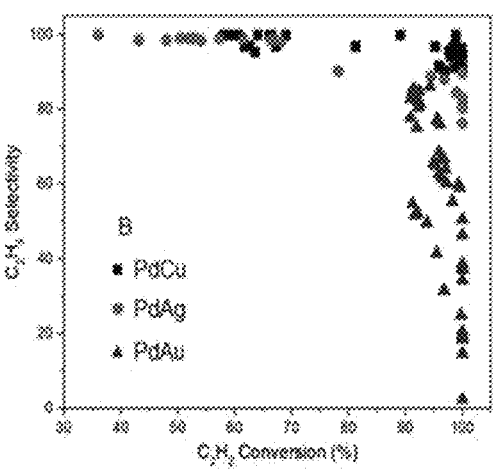

PROCESS OF SELECTIVELY HYDROGENATING GAS MIXTURE HAVING HIGH ACETYLENE CONTENT

CROSS REFERENCE TO RELATED APPLICATION

This application claims priority to Korean Patent Application No. 10-2021-0144229, filed Oct. 27, 2021, the disclosure of which is hereby incorporated by reference in its entirety.

BACKGROUND OF THE INVENTION

Field of the Invention

The present disclosure relates to a process for the selective hydrogenation of a gas mixture having high acetylene content. More particularly, the present disclosure is directed to a process for converting methane into value-added compounds, in which a gas mixture containing hydrogen as well as high-concentration acetylene formed through methane pyrolysis (e.g. non-oxidative coupling of methane) is selectively hydrogenated in the presence of a bimetallic supported catalyst to obtain ethylene from acetylene in the gas mixture while unreacted methane and hydrogen are recovered as byproducts and/or additionally recycled.

Description of Related Art

Methane is the most abundant compound in natural gas, and accounts for twice the amount of carbon as other known fossil fuel sources. Specifically, it has been reported that natural gas reserves are more extensive than those of coal and oil put together. With the gradual depletion of coal and oil, the utilization of natural gas is having a significant impact on the global energy balance. That is, because methane reserves of natural gas are more extensive than those for petroleum resources, methane is emerging as the most realistic alternative raw material to replace petroleum due to depletion of petroleum resources. Thorough research on technologies for converting methane into heavier value-added materials, such as ethylene, benzene, naphtha, fuel oil, etc., is ongoing.

A direct conversion method and an indirect conversion method are known methods for converting methane into heavier hydrocarbons. The indirect conversion method mainly involves the production of synthesis gas through steam reforming, etc., while the direct conversion method does not involve an intermediate step such as one for the production of synthesis gas. Currently, most commercialized value-added processes for methane synthesize hydrocarbon compounds from synthesis gas generated through partial oxidation of methane. For example, in the Fischer-Tropsch process, hydrocarbons and the like are produced from synthesis gas using a metal catalyst (Co, Fe). However, this indirect conversion technology requires several steps to be performed, so the reaction efficiency is low, and it is difficult to attain economic feasibility in certain regions owing to high processing costs attributable to high-temperature and high-pressure operating conditions.

As an alternative thereto, a method of directly converting methane, without the need to produce synthesis gas, has been proposed. Typically, production of C2+ hydrocarbons (e.g. C2 hydrocarbons such as ethane, ethylene, and/or acetylene and aromatics such as benzene) through oxidative coupling of methane has been proposed (e.g. Korean Patent Application Publication No. 10-2018-0113448). Another direct methane conversion route is to produce C2+ hydrocarbons using a non-oxidative route. However, the direct conversion method described above has a tendency to form byproducts. In the oxidative conversion route, carbon oxides ($CO$, $CO_2$, etc.) may be formed, and in the non-oxidative conversion route, cokes, which causes deactivation of the catalyst, may be formed.

Nevertheless, researches for solving problems such as coke formation while maximizing the advantages of the direct conversion method are underway. In this regard, the present inventors have attempted at increasing the conversion of methane and suppressing coke formation by more precisely controlling reaction conditions including a ratio of hydrogen to methane, a pyrolysis temperature, a reaction pressure, a residence time, and the like in the presence of the added hydrogen during methane pyrolysis. Here, when methane pyrolysis is performed under controlled reaction conditions in order to increase the conversion of methane and maximally suppress coke formation, acetylene may be mainly produced as a C2 hydrocarbon, and a gaseous product remaining after separation of aromatics (e.g., benzene) from pyrolysis products is a product containing acetylene at a high concentration. Moreover, when maximizing the conversion of methane during the pyrolysis, economic efficiency increases, but coke is formed in excess, and thus operation becomes impossible. Even upon operation with desirable methane conversion, methane pyrolysis products necessarily contain hydrogen and unreacted methane. As such, the methane pyrolysis products obtained after separation of aromatics have higher acetylene concentration than any conventional methane pyrolysis products. The pyrolysis products containing high-concentration acetylene may be obtained even when the pyrolysis is performed using a high-temperature plasma reactor under controlled reaction conditions in order to increase the conversion of methane and suppress coke formation, but there is a disadvantage in that the use of the plasma reactor makes it difficult to ensure economic feasibility. Meanwhile, reported acetylene conversion catalysts useful for hydrogenating acetylene to ethylene contain a platinum-supported catalyst, a palladium-supported catalyst, etc., but these conventional catalysts are limited in increasing the conversion of acetylene in the pyrolysis products containing high-concentration acetylene and the selectivity for ethylene. Furthermore, the hydrogen-to-acetylene ratio is equivalent in the conventional acetylene conversion process, but the hydrogen-to-acetylene ratio is high in the pyrolysis products.

In addition, methane pyrolysis products contain a considerable amount of hydrogen. Hydrogen has high energy efficiency per unit mass, and generates only water upon combustion, without any other harmful byproducts. Based on these advantageous characteristics, the value of hydrogen as a clean energy source has increased recently. If hydrogen formed as a byproduct of the dehydrogenation during methane pyrolysis is effectively recovered, it would be advantageous in view of improving the economic feasibility of the entire process.

Therefore, a selective hydrogenation catalyst capable of maximizing the yield of ethylene from methane pyrolysis products having high acetylene content, particularly having a composition hardly containing ethylene, compared to the conventional techniques using non-oxidative coupling of methane, and a method capable of increasing the utilization of hydrogen in the pyrolysis products are required.

SUMMARY OF THE INVENTION

An embodiment of the present disclosure is intended to provide a method of producing ethylene at high yield through selective hydrogenation of a gas mixture containing high-concentration acetylene resulting from a methane pyrolysis process.

Another embodiment of the present disclosure is intended to provide a method of effectively recovering or utilizing hydrogen as well as ethylene from methane pyrolysis products. An aspect of the present disclosure provides a selective hydrogenation method comprising the steps of:

step a) providing a gas mixture containing at least 2 mol % of acetylene, at least 50 mol % of hydrogen, and up to 48 mol % of methane, step b) forming a hydrogenation product having an increased ethylene concentration compared to the gas mixture by hydrogenating the gas mixture in the presence of a hydrogenation catalyst in which a first metal $M_1$ having hydrogenation activity and a second metal $M_2$ having a function of inducing selective hydrogenation are loaded on a porous support, and step c) separating and recovering ethylene and hydrogen from the hydrogenation product, in which the first metal $M_1$ is at least one selected from the group consisting of Pd, Pt, Rh, Ir, Ni, and Co, and the second metal $M_2$ is at least one selected from the group consisting of Cu, Ag, Au, Zn, Ga, and Sn, and the amounts of the first metal $M_1$ and the second metal $M_2$ in the hydrogenation catalyst are 0.15 to 2 wt % and 0.8 to 30 wt %, respectively, and satisfy Equation 1 below:

$$1 < \frac{W_{M2}}{W_{M1}} < 20 \quad \text{[Equation 1]}$$

wherein $W_{M1}$ is the wt % of the first metal in the hydrogenation catalyst and $W_{M2}$ is the wt % of the second metal in the hydrogenation catalyst.

According to an exemplary embodiment, the gas mixture may contain 3 to 10 mol % of acetylene, 52 to 75 mol % of hydrogen, and 18 to 45 mol % of methane.

According to an exemplary embodiment, the gas mixture may further contain C2 hydrocarbons other than acetylene, the concentration thereof being less than 1 mol %.

According to an exemplary embodiment, the gas mixture may further contain at least one selected from the group consisting of C3 to C5 hydrocarbons, the concentration thereof being less than 1 mol %.

According to an exemplary embodiment, step b) may be performed without any external hydrogen supply.

According to an exemplary embodiment, the first metal $M_1$ may have hydrogen adsorption energy of −4 to −2 eV, and the second metal $M_2$ may have hydrogen adsorption energy of −1 to 0 eV.

According to an exemplary embodiment, the first metal $M_1$ and the second metal $M_2$ in the hydrogenation catalyst may be palladium (Pd) and copper (Cu), respectively.

According to an exemplary embodiment, the porous support in the hydrogenation catalyst may be at least one selected from the group consisting of alumina, silica, carbon, zirconia, titania, ceria, and silicon carbide.

According to an exemplary embodiment, the hydrogenation catalyst may be prepared by a method comprising: preparing a precursor solid by spray impregnating a support with a solution of a composite precursor in which a precursor of the first metal $M_1$ and a precursor of the second metal $M_2$ are combined.

According to an exemplary embodiment, the method of preparing the hydrogenation catalyst may further comprise reducing the precursor of the first metal $M_1$ and the precursor of the second metal $M_2$ in the precursor solid at a temperature of 200 to 400° C. in a reducing atmosphere.

BRIEF DESCRIPTION OF THE DRAWINGS

The above and other objects, features, and other advantages of the present invention will be more clearly understood from the following detailed description taken in conjunction with the accompanying drawings, in which:

FIG. 8A is a graph showing the yield of hydrocarbons produced through methane pyrolysis and hydrogenation using a PdCu catalyst (pyrolysis conditions: 1235° C., 0.5 bar, $H_2/CH_4=1$, and GHSV=1415 $hr^{-1}$; hydrogenation conditions: 100° C., 0.5 bar, WHSV=4 L/g hr), and FIG. 8B is a graph showing the selectivity for ethylene using each of a PdCu catalyst, a PdAg catalyst, and a PdAu catalyst (in which the temperature for a catalytic reactor is changed to control the conversion of acetylene).

DESCRIPTION OF THE INVENTION

Figure 1:
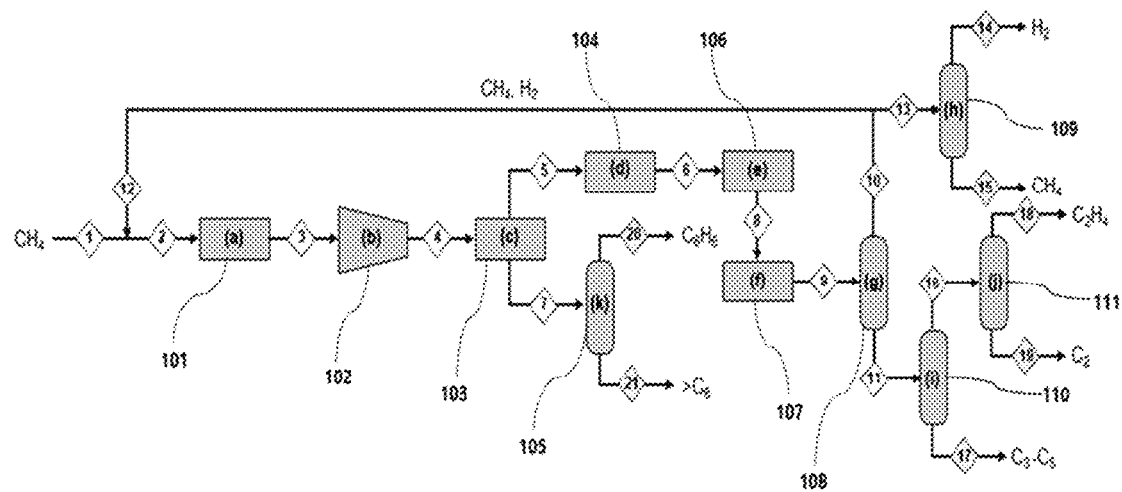
FIG. 1 schematically shows a process of producing ethylene through combination of a methane pyrolysis process and an acetylene hydrogenation process.

The present invention can be worked in its entirety based on the following description. It should be understood that the following description is given of preferred embodiments of the present invention, and the present invention is not necessarily limited thereto. In addition, the accompanying drawings are provided to aid understanding of the present invention, and the present invention is not limited thereto.

Terms used herein may be defined as follows.

The term "coke" may refer to a hydrocarbon having low hydrogen content, particularly a residual solid carbon byproduct.

The term "coupling" may refer to a chemical reaction in which two identical molecules react to form a larger molecule in a narrow sense.

The term "methane coupling" may refer to a reaction that forms not only C2 hydrocarbons (e.g. ethane, ethylene, acetylene, etc.) from methane, but also larger hydrocarbons ($C_{2+}$) (e.g. benzene, naphthalene, etc.).

The term "pyrolysis" may refer to a reaction in which hydrocarbons are decomposed upon exposure to heat or the like even without the addition of oxygen or oxygen-containing reactants, and in the present disclosure, may be construed to include a reaction that converts a compound into one or more other materials by applying heat thereto.

The term "heterogeneous catalyst" may refer to a catalyst that exists in a phase different from that of a reactant during a catalytic reaction, for example, a catalyst that is not dissolved in a reaction medium. For a heterogeneous catalyst, in order for the reaction to occur, at least one reactant has to be diffused and adsorbed to the surface of the heterogeneous catalyst, and after the reaction, the product needs to be desorbed from the surface of the heterogeneous catalyst.

The term "support" may refer to a material (typically a solid material) having a high specific surface area, and onto which a catalytically active component is attached or deposited.

The term "hydrogenation" may refer to a reaction in which hydrogen content in a compound is increased by chemically adding hydrogen to at least a portion of the compound by bringing the compound into contact with a catalyst in the presence of hydrogen.

The term "impregnation" may refer to a method of preparing a catalyst by impregnating a support with a solution in which a catalyst precursor is dissolved and then performing drying and/or firing (or reduction treatment) as necessary.

The term "conversion" may refer to the number of moles of the feedstock that are converted into a compound other than the feedstock per unit mole thereof.

The term "selectivity" may refer to the number of moles of a target product per unit mole of the converted feedstock.

According to an embodiment of the present disclosure, there is provided a process of selectively converting acetylene into ethylene by hydrogenating a gas mixture. The gas mixture may typically be a methane pyrolysis product, particularly a gas mixture remaining after separating C6 or higher hydrocarbons, especially aromatic hydrocarbons, among pyrolysis products of methane. Accordingly, the gas mixture may be substantially free of aromatic hydrocarbons such as benzene, toluene, naphthalene, and the like.

According to an embodiment, the gas mixture, which is a feedstock for the hydrogenation reaction, may contain acetylene at a relatively high concentration compared to conventional methane pyrolysis products. As such, the gas mixture containing high-concentration acetylene results from a phenomenon by which methane is mainly converted into acetylene rather than ethylene upon pyrolysis in the presence of hydrogen, under controlled pyrolysis reaction conditions (temperature, pressure, residence time, etc.) for the purpose of increasing the conversion of methane and maximally suppressing coke formation during the pyrolysis. The gas mixture having such a composition may be obtained from a non-oxidative pyrolysis product of methane (particularly, a non-oxidative methane coupling product), a plasma pyrolysis (or coupling) product of methane, and combinations thereof. In particular, the gas mixture applicable in this embodiment is derived from typical methane pyrolysis, particularly a pyrolysis reaction that does not use oxygen (non-oxidative pyrolysis), and is thus substantially free of carbon monoxide, carbon dioxide, etc.

According to an embodiment, the concentration of acetylene in the gas mixture may be at least about 2 mol %, particularly about 3 to 10 mol %, and more particularly about 4 to 8 mol %. The concentration of acetylene set forth above is distinguished from that in conventional methane pyrolysis products in which the concentration of acetylene is less than about 2 mol % (particularly about 0.5 to 1 mol %) and the concentration of C2 hydrocarbons other than acetylene, such as ethane and ethylene, is relatively high.

The gas mixture may further comprise hydrogen that is formed as a byproduct through a C—C coupling reaction during methane pyrolysis and/or hydrogen that is supplied or reacted together with methane for the purpose of increasing the conversion and suppressing coke formation during methane pyrolysis, as described below. By way of example, the gas mixture may contain hydrogen in an amount of at least about 50 mol %, particularly about 52 to 75 mol %, and more particularly about 60 to 65 mol %. Moreover, the gas mixture may typically contain unconverted methane (i.e. unreacted methane) in the pyrolysis reaction. For instance, the concentration of methane is up to about 48 mol %, particularly about 18 to 45 mol %, and more particularly about 28 to 35 mol %.

According to a particular embodiment, the gas mixture may contain about 4 to 7 mol % of acetylene, about 62 to 64 mol % of hydrogen, and about 30 to 33 mol % of methane.

According to an exemplary embodiment, the gas mixture may further contain C2 hydrocarbons other than acetylene. Here, C2 hydrocarbons may be ethane and/or ethylene. The concentration of C2 hydrocarbons other than acetylene may be, for example, less than about 1 mol %, particularly less than about 0.75 mol %, and more particularly less than about 0.5 mol %. According to a particular embodiment, the concentration of ethylene in the gas mixture may be, for example, less than about 1 mol %, particularly less than about 0.75 mol %, and more particularly less than about 0.5 mol %.

Also, according to an exemplary embodiment, the gas mixture may further contain hydrocarbons, for example C3 to C5 hydrocarbons, remaining after separation of aromatics from methane pyrolysis products. Such hydrocarbons may typically be contained at a concentration of less than about 1 mol %, particularly less than about 0.75 mol %, and more particularly less than about 0.5 mol %.

According to an embodiment, acetylene in the gas mixture may be converted into ethylene through a selective hydrogenation using a catalyst. Notably, the hydrogen contained in the gas mixture may be utilized as it is without the need to separately or externally supply hydrogen necessary for the hydrogenation of acetylene. Although hydrogen supplementation from any external sources to reach a hydrogen partial pressure suitable for effective hydrogenation of acetylene is not strictly excluded, the amount of hydrogen that is added may be greatly decreased in such cases. In this regard, the $H_2/C_2H_2$ molar ratio in the reaction product for the selective hydrogenation of acetylene to ethylene may be suitably adjusted within the range of, for example, about 5 to 35, particularly about 8 to 30, more particularly about 9 to 20, and much more particularly about 10 to 15.

Meanwhile, the hydrogenation may be carried out in the presence of a catalyst. Here, it is necessary to use a catalyst having activity capable of increasing the conversion of acetylene and the selectivity for ethylene in a gas mixture having high acetylene concentration compared to typical pyrolysis products. To this end, in this embodiment, a hydrogenation is carried out in the presence of a heterogeneous catalyst in which at least two metals, particularly a first metal $M_1$ having hydrogenation activity and a second metal $M_2$ having a function of inducing selective hydrogenation, are loaded or supported on a porous support. Since this metal function may be quantified with H adatom adsorption energy through DFT (density functional theory) calculations, the first metal $M_1$ may exhibit hydrogen adsorption energy of about −4 to −2 eV and the second metal $M_2$ may exhibit hydrogen adsorption energy of −1 to 0 eV.

The first metal $M_1$ may be at least one selected from the group consisting of Pd, Pt, Rh, Ir, Ni, and Co, and particularly may be Pd. Also, the second metal $M_2$ may be at least one selected from the group consisting of Cu, Ag, Au, Zn, Ga, and Sn, and particularly may be Cu. According to a particular embodiment, the combination of metals supported on the support may be a combination of Pd and Cu, and the reason for use thereof may be explained by the alloying effect. The hydrogenation catalyst used in this embodiment is a catalyst comprising two types of active metal components, and the first metal (particularly Pd) and the second metal (particularly Cu) may be in a state showing crystallinity, and may also be in an alloy form or in a supported form while intimately or closely contact with each other. In addition, the first metal $M_1$ may exist in the form of a single atom, and the second metal $M_2$ may exist in the form of nanoparticles.

In an exemplary embodiment, the size of the active metals (or each of the first and second metals) in the hydrogenation catalyst may be, for example, about 100 nm or less, particularly about 10 to 70 nm, and more particularly about 20 to 50 nm.

According to an embodiment, the amount of the first metal $M_1$ in the hydrogenation catalyst may be, for example, about 0.15 to 2 wt %, particularly about 0.2 to 1 wt %, and more particularly about 0.21 to 0.5 wt %. Since the amount of the first metal affects selective hydrogenation activity and selectivity, it may be advantageously controlled within the above range. Also, the amount of the second metal $M_2$ may be, for example, about 0.8 to 30 wt %, particularly about 1 to 10 wt %, and more particularly about 1.5 to 5 wt %. If the amount of the second metal is excessively high or low, activity may be insufficient, or nonselective hydrogenation may be induced. Hence, the amount of the second metal may be set within the above range.

Meanwhile, in an exemplary embodiment, the first metal $M_1$ and the second metal $M_2$ may be combined at a predetermined ratio depending upon the properties of each metal. In this regard, the hydrogenation catalyst may satisfy Equation 1 below (based on ICP-OES analysis).

$$1 < \frac{W_{M2}}{W_{M1}} < 20 \qquad \text{[Equation 1]}$$

In Equation 1, $W_{M1}$ is the wt % of the first metal in the hydrogenation catalyst and $W_{M2}$ is the wt % of the second metal in the hydrogenation catalyst.

According to an exemplary embodiment, $$\frac{W_{M2}}{W_{M1}}$$

may be adjusted within the range of, for example, about 2 to 10, particularly about 3 to 8, and more particularly about 4 to 7. If the amount of the first metal $M_1$ relative to the second metal $M_2$ falls outside a predetermined range, activity may be remarkably deteriorated, or a phenomenon by which selectivity for acetylene decreases during the hydrogenation may occur. Hence, each amount of the active metal components may be appropriately adjusted to fall within the above range.

Meanwhile, the support for loading the two metals (the first and second metals) may be at least one selected from the group consisting of alumina, silica, carbon, zirconia, titania, ceria, and silicon carbide. Particularly, alumina, and more particularly gamma-alumina, may be used.

According to an exemplary embodiment, the support may be a porous support, and the porosity of the support may be controlled such that the reactant or product does not remain for an excessively long time when diffusing in the support.

In this regard, the support may exhibit properties exemplified below:
  Specific surface area (BET): at least about 300 m²/g, particularly about 400 to 700 m²/g, and more particularly about 500 to 600 m²/g;
  Pore volume: at least about 0.5 cm³/g, particularly about 0.75 to 2 cm³/g, and more particularly about 1 to 1.5 cm³/g; and
  Average pore size: about 50 to 200 Å, particularly about 70 to 180 Å, and more particularly about 100 to 150 Å.

Moreover, according to an exemplary embodiment, the support may be prepared in various shapes known in the art, as well as in a powder form. Examples thereof may include a spherical shape (including a hollow shape), a cylindrical shape (including a hollow shape), a granular shape, a tablet shape, a ring shape, a saddle shape, a star shape, a honeycomb shape, a pellet shape, a trilobe shape, a quadrilobe shape, and the like. As such, for illustrative purposes, in order to prepare a support having a specific shape, a molding method known in the art, extrusion, spray drying, pelletizing, oil dropping, etc. may be performed. Also, the average size of the support having a shape exemplified above may be in the range of, for example, about 1 to 5 mm, particularly about 1.5 to 3 mm, and more particularly about 2 to 2.75 mm, which are understood for illustrative purposes.

According to an exemplary embodiment, the hydrogenation catalyst may be prepared through any loading techniques known in the art, examples of which may include impregnation, deposition, ion-exchange, deposition-precipitation, etc. Particularly, the impregnation, and more particularly, incipient wetness impregnation or modified incipient wetness impregnation, may be applied.

In a particular embodiment, the catalyst may be prepared through an impregnation technique. To this end, the metal may be used in the form of a precursor, particularly a metal compound, more particularly a metal salt, a complex, etc., and may be selected from among types that are soluble in the medium used to prepare the impregnation solution (particularly, an aqueous medium). For example, when the first metal among the active metals is palladium, a precursor thereof may be an organic acid salt or an inorganic acid salt, a complex, a hydroxide, a halide, or a combination thereof. For example, a palladium precursor may be at least one selected from among palladium acetate, palladium chloride, palladium nitrate, palladium ammonium nitrate, palladium sulfate, palladium carbonate, palladium hydroxide, palladium halide, hydrates thereof, and the like, which are understood for illustrative purposes. More typically, palladium ammonium nitrate may be used as the precursor. On the other hand, when the second metal is copper, the precursor thereof may be at least one selected from among, for example, copper hydroxide phosphate, copper nitrate, copper sulfate, copper acetate, copper formate, copper (II) chloride, copper iodide, and the like, and more typically, copper nitrate may be used.

According to an exemplary embodiment, the impregnation solution may be prepared by sequentially or simultaneously adding the first metal precursor and the second metal precursor to the medium. Here, the total concentration of the active metal precursors (the first metal precursor and the second metal precursor) in the impregnation solution may be adjusted within the range of, for example, about 0.01 to 2 μM, particularly about 0.1 to 1 μM, and more particularly about 0.25 to 0.75 μM, depending upon the amounts of the first and second metals that are supported in the final catalyst and the ratio between the first metal and the second metal. In addition, the pH of the solution containing the first metal precursor and the second metal precursor may be adjusted within the range of, for example, about 1 to 3, particularly about 1.2 to 2, and more particularly about 1.3 to 1.5, in order to effectively disperse the metal precursor in the support. To this end, an acid component known in the art may be added to the impregnation solution. Such an acid component may be at least one selected from among nitric acid, sulfuric acid, hydrochloric acid, oxalic acid, and the like.

The impregnation process is not limited to a particular process, so long as the metal precursor solution (i.e. the composite precursor solution of the first and second metals) is able to sufficiently contact the pores in the support. For example, the metal precursor solution may be sprayed for contact or impregnation, thus forming a precursor solid. Alternatively, the support may be immersed in the metal precursor solution, for example, at about 15 to 80° C. (particularly at about 20 to 50° C., more particularly at room temperature) for about 0.5 to 3 hours (particularly about 1 to 2 hours). However, these conditions are set forth for illustrative purposes.

After impregnation of the support with the active metals as described above, a drying process may be performed, for example, under an oxygen-containing atmosphere (particularly, ambient air). Here, the drying temperature may be set within the range of, for example, about 60 to 150° C., particularly about 70 to 100° C., but is not limited thereto. Also, the drying time may be set within the range of, for example, about 3 to 24 hours, particularly about 6 to 12 hours. Through the drying process, the metal precursor may be more closely attached to the support. Ultimately, there may be provided a structure in which the support is covered with the active metal precursors, for example is, a core-shell structure.

After the solid in which the first metal precursor and the second metal precursor are attached or deposited onto the support is obtained as described above, the metal component may be converted into a reduced or elemental form through reduction treatment. Here, although calcination or heat treatment before reduction treatment is not excluded, the reduction treatment of the precursor solid without calcination may be adopted.

The reduction treatment may be performed using hydrogen alone or hydrogen diluted with an inert gas (e.g. $N_2$, He, Ar, etc.), and may be carried out in the temperature range of, for example, about 200 to 400° C., particularly about 220 to 380° C., and more particularly about 250 to 350° C. Here, the heating rate may be set within the range of, for example, about 3 to 10° C./min, particularly about 4 to 8° C./min, and more particularly about 5 to 7° C./min. Also, the reduction treatment time is not particularly limited, and may be adjusted within the range of, for example, about 0.5 to 24 hours, particularly about 1 to 12 hours. Illustratively, when the reducing gas is diluted with the inert gas, the concentration of the reducing gas may be in the range of, for example, about 5 to 20 vol %. In addition, the pressure during the reduction treatment may be in the range of, for example, approximately atmospheric pressure to 10 bar (typically atmospheric pressure).

According to an embodiment, the gas mixture containing high-concentration acetylene is hydrogenated in the presence of the catalyst described above. Here, the hydrogenation temperature may be set within the range from room temperature to 250° C., particularly about 40 to 200° C., and more particularly about 50 to 150° C. Also, the hydrogenation pressure may be set within the range of, for example, about 0.2 to 1 bar, particularly about 0.3 to 0.8 bar, and more particularly about 0.4 to 0.7 bar.

According to an exemplary embodiment, the hydrogenation may be performed in a batch or continuous mode, but a continuous mode is preferable in terms of economic feasibility of operation and the like. Here, the reactor is not particularly limited, but, for example, a gaseous fixed-bed reactor, a fluidized-bed reactor, etc. may be used, and a fixed-bed reactor may be advantageously used. Moreover, the gas hourly space velocity (GHSV) is determined depending upon both the productivity of ethylene and the conversion through catalytic contact. If the gas hourly space velocity is excessively low, productivity may be deteriorated, whereas if the gas hourly space velocity is excessively high, contact with the catalyst may become insufficient. In consideration thereof, the gas hourly space velocity may be adjusted within the range of, for example, about 1 to 15 $L/g_{cat}\cdot hr^{-1}$, particularly about 2 to 10 $L/g_{cat}\cdot hr^{-1}$, and more particularly about 3 to 5 $L/g_{cat}\cdot hr^{-1}$.

According to an exemplary embodiment, the conversion of acetylene in the gas mixture as the feedstock may be in the range of, for example, at least about 95%, particularly at least about 97.5%, and more particularly about 99 to 99.9%, and also, the selectivity for ethylene may be in the range of, for example, at least about 95%, particularly at least about 97.5%, and more particularly about 99 to 99.9%. Here, the above numerical ranges are understood for illustrative purposes.

The hydrogenation product may be separated or purified using a combination of techniques known in the art (e.g. distillation, PSA, etc.) to thus recover ethylene and hydrogen therefrom. However, the hydrogenation product may still contain methane and hydrogen remaining after the hydrogenation, and methane and a portion of hydrogen may be recycled during the separation. Here, methane and hydrogen may be recycled individually or in the form of a mixed gas. For example, methane and hydrogen may be recycled in the form of a mixed gas and introduced into a pyrolysis reactor together with a fresh methane-containing feedstock (or a combination thereof with hydrogen). In this case, the $CH_4/H_2$ molar ratio in the recycle flow may be adjusted within the range of, for example, about 0.05 to 1, more particularly about 0.1 to 0.8, and more particularly about 0.2 to 0.5.

Combination of Pyrolysis and Hydrogenation

An exemplary process for producing ethylene by combining a methane pyrolysis process and an acetylene hydrogenation is shown in FIG. 1. This example is provided to deepen understanding of the present disclosure, and in particular, the pyrolysis process before the hydrogenation may be implemented in various ways, and is not necessarily limited to the embodiment as exemplified below.

With reference to the above drawing, a methane-containing gas 1 as a feedstock is introduced into a pyrolysis reactor 101 as a gas mixture 2 of methane and hydrogen combined with a recycled mixed gas (a mixed gas of methane and hydrogen; 12). For example, the methane-containing gas 1, which is composed exclusively of methane or contains not only methane but also a diluent gas, may be introduced into the pyrolysis reactor 101. For example, the diluent gas may be at least one selected from the group consisting of nitrogen, carbon dioxide, and hydrogen sulfide, the amount of which may be at most about 20 mol %, particularly up to about 10 mol %, more particularly up to about 5 mol %, and much more particularly up to about 3 mol %, but the above ranges are set forth for illustrative purposes.

Here, the pyrolysis reactor is not limited to a specific type, but may be a radial tube reactor due to its good heat transfer efficiency. Moreover, the material for a pyrolysis reactor, particularly a non-oxidative direct conversion reactor, may be at least one selected from among alumina, SiC, FeCrAl alloy, Inconel (NiCr), and the like.

Meanwhile, methane is a non-polar molecule similar to the stable structure of an inert gas, and the binding energy of C—H is 435 kJ/mol, and the thermodynamic stability thereof is high. High chemical and thermodynamic stability makes it difficult to convert methane into various compounds. According to the present embodiment, C2+ hydrocarbons and hydrogen byproducts are generated from methane through a direct non-oxidative coupling reaction or a plasma coupling reaction in the pyrolysis process. Hereinafter, a pyrolysis process involving a direct non-oxidative coupling reaction is mainly described.

For the pyrolysis, a radical reaction is carried out after methane is activated to a methyl radical. The reaction temperature and pressure conditions may be sophisticatedly controlled to increase the conversion of methane and suppress coke formation. By way of example, the pyrolysis temperature may be adjusted within the range of, for example, about 1000 to 1400° C., particularly about 1050 to 1350° C., more particularly about 1100 to 1300° C., and much more particularly about 1150 to 1250° C. Also, the pyrolysis pressure may be adjusted within the range of, for example, about 0.1 to 1 bar, particularly about 0.2 to 0.8 bar, more particularly about 0.3 to 0.7 bar, and much more particularly about 0.4 to 0.6 bar. Also, the gas hourly space velocity (GHSV) may be set within the range of, for example, about 300 to 3600 $hr^{-1}$, particularly about 720 to 1800 $hr^{-1}$, more particularly about 900 to 1600 $hr^{-1}$, and much more particularly about 1200 to 1440 $hr^{-1}$.

In the illustrated embodiment, as described above, the recycled mixed gas introduced into the reactor together with the fresh methane-containing feedstock contains methane and hydrogen, and thus a pyrolysis reaction occurs in the presence of hydrogen, which is effective at increasing the conversion of methane and suppressing the formation of coke materials. Under these reaction conditions, methane may be mainly converted into acetylene rather than ethylene, among C2 hydrocarbons. In this regard, the composition of the materials within the pyrolysis reactor may satisfy the requirement represented by Equation 2 below.

$$\frac{P_{H_2}}{P_{CH_4}} \geq 0 \quad \text{[Equation 2]}$$

wherein, $P_{H2}$ is the partial pressure of hydrogen in the mixed gas introduced into the reactor and $P_{H4}$ is the partial pressure of methane in the mixed gas introduced into the reactor.

According to an exemplary embodiment, $$\frac{P_{H_2}}{P_{CH_4}}$$

may be adjusted within the range of, for example, about 0.5 to 3, particularly about 0.7 to 2.5, and more particularly about 0.9 to 1.5.

According to an exemplary embodiment, the pyrolysis may be carried out in the presence of a catalyst (e.g. a supported catalyst), and a metal having a methane activation function may be at least one selected from among iron (Fe), chromium (Cr), vanadium (V), molybdenum (Mo), tungsten (W), and the like. Also, the support that is used may be a porous support made of an inorganic oxide material, for example, at least one selected from among alumina, silica, titania, zirconia, magnesia, ceria, and the like. Also, the amount of the active metal in the catalyst may be adjusted within the range of, for example, about 0.1 to 10 wt %, particularly about 0.3 to 8 wt %, and more particularly about 0.5 to 5 wt %. The catalyst composition described above is provided for illustrative purposes, and the present disclosure is not necessarily limited thereto.

According to an exemplary embodiment, the conversion of methane resulting from the pyrolysis under the reaction conditions described above may be in the range of about 10 to 50%. Here, the lower the methane conversion, the higher the selectivity for C2+ hydrocarbons. For example, the selectivity for C2+ hydrocarbons in the methane conversion range of 0 to 10% may be at least about 99.9%, the selectivity for C2+ hydrocarbons in the methane conversion range of 10 to 20% may be at least about 99.5%, the selectivity for C2+ hydrocarbons in the methane conversion range of 20 to 30% may be at least about 95%, the selectivity for C2+ hydrocarbons in the methane conversion range of 30 to 40% may be at least about 90%, and the selectivity for C2+ hydrocarbons in the methane conversion range of 40 to 50% may be at least about 80%. If the methane conversion is excessively increased, the selectivity for C2+ hydrocarbons may be lowered to about 70%, whereas if the methane conversion is excessively decreased, the yield may be insufficient. Accordingly, it may be advantageous to maintain the methane conversion in the range of, for example, about 10 to 50%, particularly about 20 to 40%, and more particularly about 30 to 35%.

In addition, the selectivity for acetylene in the pyrolysis product may be in the range of, for example, at least about 55%, particularly at least about 60%, and more particularly about 65 to 70%, and the selectivity for aromatics (especially benzene) may be in the range of, for example, about 30% or less, particularly about 5 to 25%, and more particularly about 10 to 20%.

According to an exemplary embodiment, the pyrolysis product may further contain at least one compound selected from among ethane, ethylene, C3-C5 hydrocarbons, and the like, in addition to acetylene and aromatics, and the amount thereof may be, for example, about 40 vol % or less, particularly about 30 vol % or less, and more particularly about 20 vol % or less, based on the amount of the pyrolysis product.

Referring again to FIG. 1, the pyrolysis product 3 passes through a vacuum pump 102 to form a depressurized flow 4, followed by rapid cooling to, for example, about −20 to 25° C. (particularly about −10 to 0° C.) in a quench tower 103. In the illustrated embodiment, the gas mixture is separated into an overhead flow 5 containing $C_5^-$ hydrocarbons and hydrogen and a bottom flow 7 containing $C_6^+$ hydrocarbons (particularly benzene and hydrocarbons larger than $C_6$). Here, the bottom flow 7 is separated into benzene 20 and a heavier fraction 21 in a benzene column 105, and benzene may be recovered. On the other hand, the overhead flow 5 is a fraction containing methane, hydrogen, and acetylene as described above, and is a gas mixture which may optionally further contain C2 hydrocarbons (ethane and/or ethylene) other than acetylene, and C3-C5 hydrocarbons. This gas mixture may be introduced into an acetylene converter 104, so the selective hydrogenation of acetylene as described above may be performed.

Thereafter, a hydrogenation product 6 is pressurized to, for example, about 10 to 50 bar (particularly about 15 to 30 bar) while passing through a process gas compressor 106, and the pressurized flow 8 may be cooled to, for example, about −75 to −45° C. (particularly about −60 to −55° C.) by a cold box 107. The cooled flow 9 is transferred to a demethanizer 108, from which a mixed gas 10 of methane and lighter hydrogen is discharged as the overhead flow, while C2+ hydrocarbons 11 are discharged as the bottom flow and then separated into C2 hydrocarbons 16 and C3-C5 hydrocarbons 17 in a deethanizer 110. Thereafter, the C2 hydrocarbons 16 are separated into ethylene 18 and C2 hydrocarbons 19 other than ethylene in a C2 splitter 111. Each of the demethanizer 108, the deethanizer 110, and the C2 splitter 111 operates under cryogenic conditions.

On the other hand, the mixed gas 10 is separated into a recycle flow 12 and a recovery flow 13, and the recycle flow is combined with the methane-containing feedstock and then introduced into the pyrolysis reactor 101. The recovery flow 13 is introduced into a pressure swing adsorber 109 and separated into hydrogen 14 and methane 15.

In the above-described embodiment, since the principle of operation of the separation and purification unit after the pyrolysis reaction and the selective hydrogenation is known in the art, further description of details pertaining thereto is omitted.

According to another embodiment, the process shown in FIG. 1 may be implemented in a manner that changes the arrangement of the quench tower, vacuum pump, acetylene converter, etc. while maintaining the basic configuration thereof. For example, when the quench tower, vacuum pump, and acetylene converter are sequentially disposed downstream of the methane pyrolysis reactor, the acetylene converter may operate under a pressure of atmospheric pressure or higher. In addition, the processing units may be sequentially arranged in the order of the vacuum pump, acetylene converter, and quench tower, or in the order of the acetylene converter, vacuum pump, and quench tower. Alternatively, although the processing units may be arranged in the order of the acetylene converter, vacuum pump, and quench tower or in the order of the acetylene converter, quench tower, and vacuum pump, when C6+ hydrocarbons are fed to the acetylene conversion catalyst, the catalyst lifetime may be shortened, which may be regarded undesirable.

A better understanding of the present invention may be obtained through the following examples, which are merely set forth to illustrate the present invention and are not to be construed as limiting the scope of the present invention.

EXAMPLE

Preparation of Catalyst

A trilobe-shaped alumina support was purchased from Saint-Gobain (USA) and used without further purification. Before supporting with active metals, the support was dried overnight at 80° C. in a convection oven. Palladium ammonium nitrate (Sigma, 99.9%) as a first metal precursor, and copper nitrate (Sigma, 99.9%), gold nitrate (Sigma, 99.9%), or silver nitrate (Sigma, 99.9%) as a second metal precursor were dissolved in an acid aqueous solution (acid component: 10 wt %, nitric acid). The metals were supported using a modified incipient wetness impregnation technique, and the resulting solid was dried at 80° C. in a convection oven and reduced with hydrogen at 300° C. for 6 hours (heating rate: 5° C./min). The catalyst in which a metal alloy was supported on an alumina support was represented by x % Pdy % M (in which x and y represent the wt % of each metal, and M represents a second metal (Cu, Ag, or Au)).

Methane Pyrolysis and Hydrogenation

Figure 2:
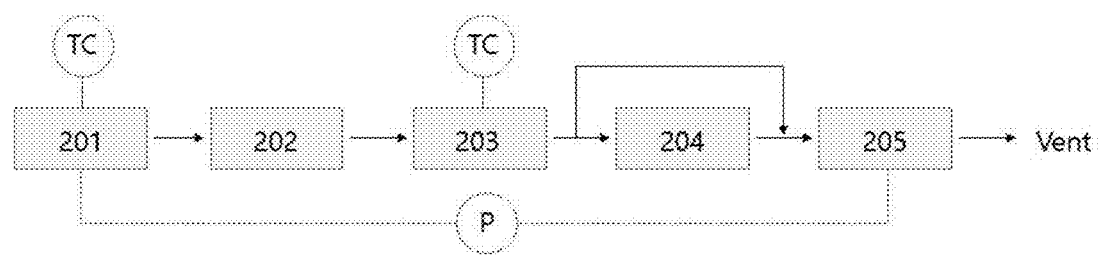
FIG. 2 schematically shows the structure of an apparatus used in Example.

Methane pyrolysis and hydrogenation were performed in a continuous flow system. The structure of the apparatus used in the present Example is schematically shown in FIG. 2.

With reference to this drawing, the experimental apparatus broadly includes a pyrolysis furnace 201, a chiller 202, a hydrogenation reactor 203, an online gas chromatograph 204, and a vacuum pump 205. The flow between the hydrogenation reactor 203 and the vacuum pump 205 was mainly used, and the above flow was changed with the online gas chromatograph 204 during analysis. Also, TC and P are a thermocouple and a pressure controller, respectively.

Specifically, in the methane pyrolysis zone, an alumina tube reactor (99.9%, ½" O.D) was disposed at the center of an electric furnace equipped with a molybdenum silicide ($MoSi_2$) heating element. Before reaction, the reactor was heat-treated at 700° C. for 2 hours under flowing air (10 mL·$min^{-1}$, 99.9%) in order to remove impurities (heating rate: 10° C./min). A gas mixture of nitrogen, methane (99.999%, Rigas), and hydrogen (UHP, Riga) was introduced into the reactor using a mass flow controller (5850E, Brooks Instrument). The pyrolysis product effluent flow was quenched at −10° C., thus collecting trace amounts of polycyclic aromatics. The quenched gas was introduced into a hydrogenation zone in which a stainless steel reactor (½" O.D, 300 mm L) was disposed at the center of an electric furnace. For all experiments, the reaction system operated below atmospheric pressure, and the reaction pressure was regulated using a vacuum controller (Buchi, V800) controlled by a diaphragm and a chemical-resistant solenoid valve (Parker). The transfer line was heated to 100° C. to prevent potential condensation. The product was sampled at intervals of 2 hours using an online gas chromatograph (Agilent Technology, 7890A) equipped with an HP-PLOT/$Al_2O_3$ capillary column (50 m×0.32 mm×8.0 mm) for FID (flame ionized detection), or with an HP-Molesieve capillary column (30 m×0.53 mm×20 mm) for TCD (thermal conductivity detection). The GC column was configured to separate hydrogen, nitrogen, and hydrocarbons in order to provide information on the conversion of methane and quantitatively analyze the concentrations of ethylene, ethane, acetylene, and benzene. The trace amounts of C3-05 products were also combined.

In addition, the microkinematic simulation used in Example was performed using the CANTERA software package.

Results and Discussion

Methane Pyrolysis Simulation

Figure 3:
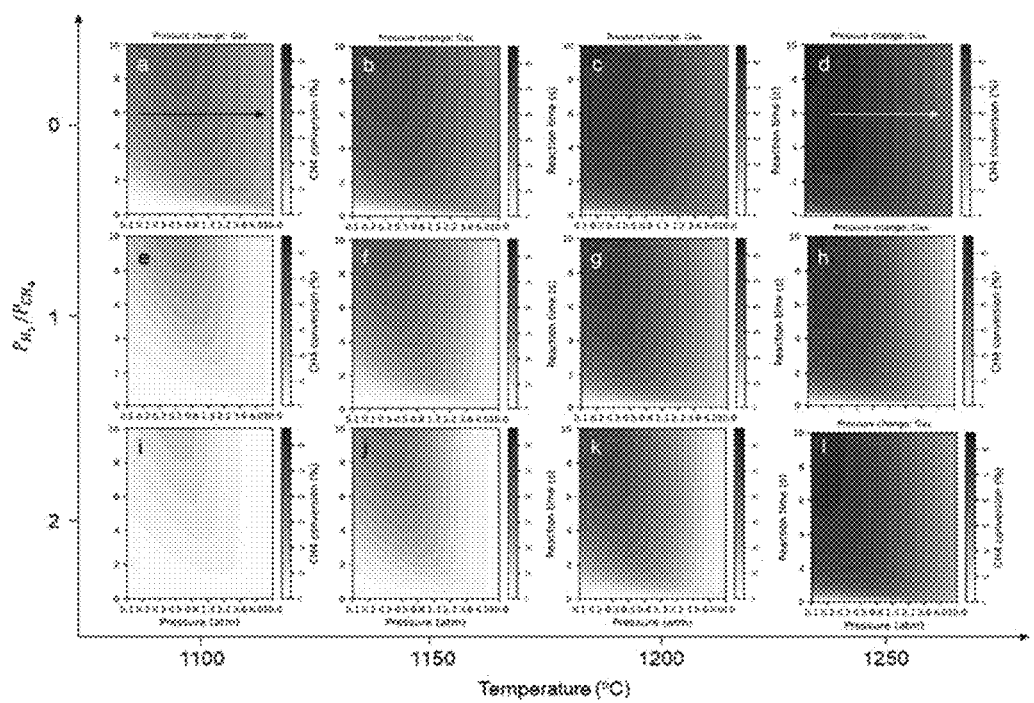
FIG. 3 includes graphs (a-l) showing the conversion of methane under different operating conditions (temperature, operating pressure, hydrogen/methane volume ratio, and residence time) (plotted as logarithmic value of reaction pressure (0.1 to 10 atm) versus residence time (sec))

In order to characterize the optimal reaction conditions for converting methane into value-added hydrocarbons as main product species, taking into consideration four reaction parameters (temperature: 1150-1250° C.; pressure: 0.1-10 bar; $H_2/CH_4$ ratio: 0-1; and residence time: 0-10 seconds), methane pyrolysis simulation was performed. The effect of each reaction parameter on the methane conversion and the product yield were plotted as contour lines in FIGS. 3 and 4. Each graph shown in FIG. 3 shows the effect of a combination of four reaction parameters. The methane conversion increased with an increase in residence time, regardless of temperature, whereas it decreased with an increase in the $H_2/CH_4$ ratio. However, the results varied depending on the operating pressure. At temperatures up to 1150° C., the methane conversion showed a volcano-shaped pattern.

As shown in graph a in FIG. 3, at 1100° C., the methane conversion started from about 45% at 0.2 bar, showed a peak value of 60% at 1 bar, and then decreased to 45% at 10 bar (residence time: 6 seconds) (black arrow). Meanwhile, at 1250° C., the methane conversion gradually decreased with an increase in the reaction pressure (yellow arrow in graph d of FIG. 3d), starting from 87% at 0.2 bar and showing 10% at 10 bar ($H_2/CH_4$=0; residence time: 6 seconds). A similar tendency was observed at 1250° C. regardless of whether hydrogen was additionally supplied (graphs d, h and l of FIG. 3). It should be noted that the operating pressure is represented as a logarithmic scale in FIG. 3 and that the methane conversion is sensitive to the reaction pressure, especially pressure lower than atmospheric pressure. In addition, the highest methane conversion was achieved below atmospheric pressure with an increase in the reaction temperature. Supposedly, this result is because the overall conversion of methane was thermodynamically inhibited by gaseous hydrogen which has been readily formed in the methane pyrolysis.

Figure 4:
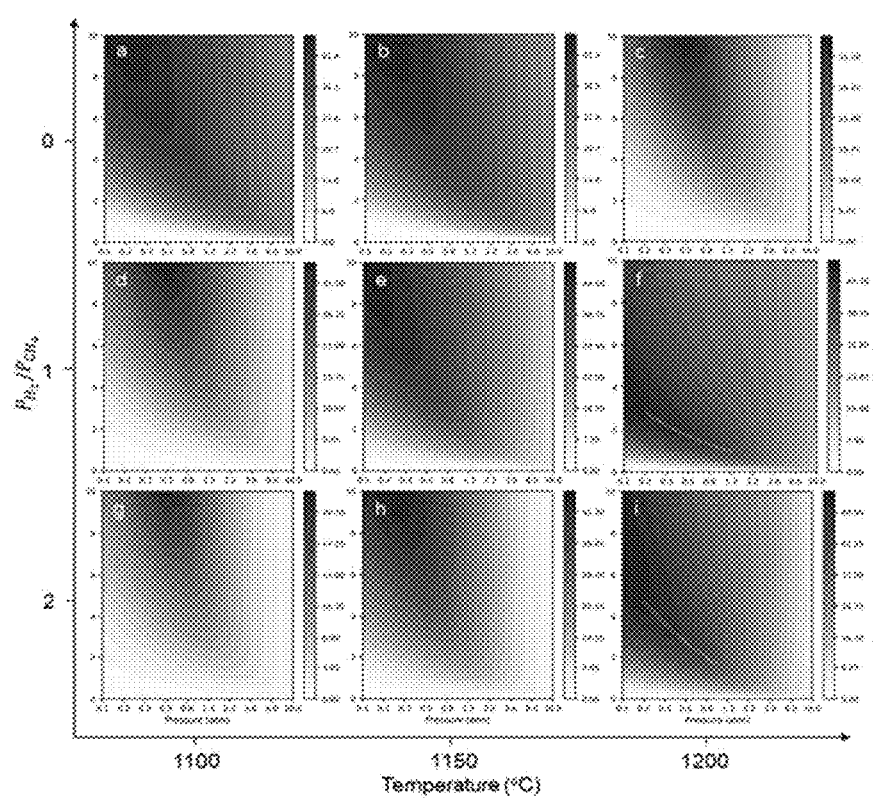
FIG. 4 includes graphs (a-i) showing the yields of C2 hydrocarbons and benzene obtained under various operating conditions.

Next, the hydrocarbon yield was reviewed, where the yields of specific hydrocarbon species (ethane, ethylene, acetylene, and benzene) were measured in the simulation, and the results thereof are shown in FIG. 4.

With the $H_2/CH_4$ ratio fixed at 0, the yield of a particular hydrocarbon product increased with an increase in the reaction pressure and residence time, regardless of temperature (yellow arrows in graphs a to c of FIG. 4). The highest hydrocarbon yield at 1100° C. occurred in a range similar to that for the highest conversion shown in graph i of FIG. 4, regardless of whether hydrogen was supplied. However, when the temperature was elevated up to 1200° C. (graph FIG. 4), the highest yield of a particular product was obtained at 0.5 bar for a residence time of 3 seconds, which is distinct from the highest observed conversion of methane (graph g of FIG. 3). These differences reflect conversion of methane into other hydrocarbons, mostly polycyclic aromatic hydrocarbons. The simulation results support the notion that controlling the reaction pressure and supplying hydrogen are important considerations in the methane pyrolysis for selectively producing heavier hydrocarbons.

Figure 5:
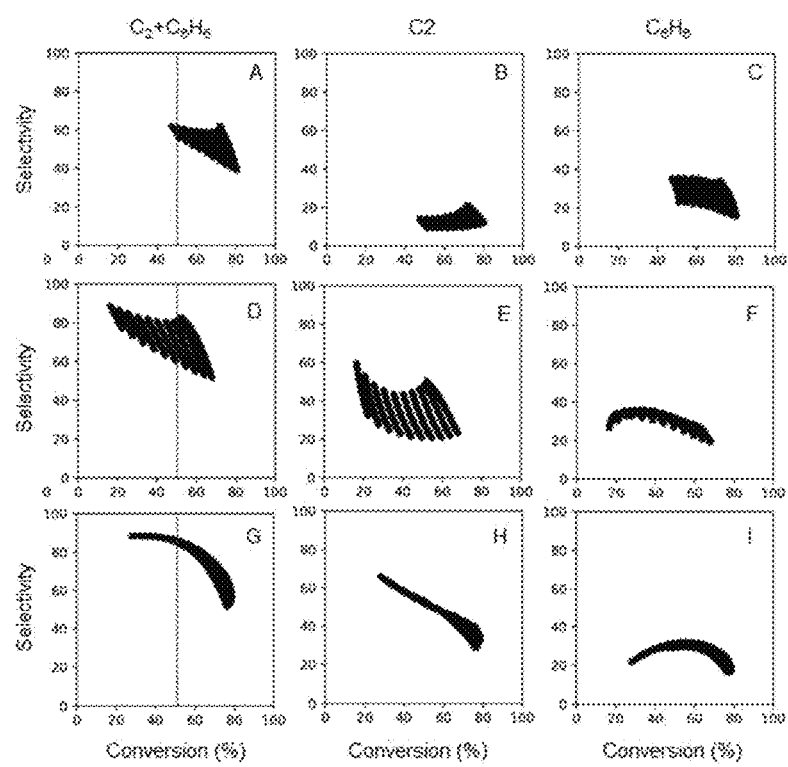
FIG. 5 shows simulation results plotting the selectivity for each of $C2+C_6H_6$ (A, D, G in FIG. 5), C2 (B, E, H in FIG. 5), and $C_6H_6$ (C, F, I in FIG. 5) versus conversion of methane when hydrogen is also supplied under different reaction pressures at a temperature of 1200° C. for a residence time of 1-5 seconds (in in A, B, C of FIG. 5, $H_2/CH_4=0$, 1-10 bar; in D, E, and F of FIG. 5, $H_2/CH_4=1$, 0.1-10 bar; and in G, H, and I, of FIG. 5, $H_2/CH_4=1$, 0-0.5 bar)

As such, the effects of low pressure and the supply of hydrocarbons and hydrogen together on the selectivity of hydrocarbons during methane pyrolysis can be confirmed by plotting conversion versus selectivity, as shown in FIG. 5. In this simulation, in order to understand the influence of the reaction pressure and hydrogen supply, experimental conditions at a predetermined temperature of 1200° C. were classified into three zones: when hydrogen was supplied (graphs A to C of FIG. 5), when hydrogen was not supplied (graphs D to I of FIG. 5), when the operating pressure was less than atmospheric pressure (graphs G to I of FIG. 5), and when the operating pressure exceeded atmospheric pressure (graphs A to F of FIG. 5).

The measured conversion of methane versus the selectivity for hydrocarbons (ethane, ethylene, acetylene, and benzene) allows prediction of the ideal product composition, which is strongly dependent on operating conditions. Comparing graphs A and D of FIG. 5, when hydrogen was supplied together, total methane conversion was decreased but selectivity for hydrocarbons was increased. For example, under normal operating conditions, C2+C6 selectivity obtainable at a methane conversion of 50% was about 60% (the dotted lines in graphs A to I of FIG. 5), but was about 80% when hydrogen was also supplied. This improvement may be deemed to be mainly due to an increase in C2 selectivity (graphs B and E of FIG. 5). This indicates that hydrogen has a significant effect of inhibiting the formation of polycyclic aromatics.

Then, when the operating pressure is set below atmospheric pressure in the methane pyrolysis, the selectivity range for the methane conversion may be narrowed. For example, for a methane conversion of about 50%, selectivity was 60 to 80% at 1 to 10 bar, but was about 85% at 0.1 to 0.5 bar. These distinct results suggest that, when the operating pressure is adjusted below atmospheric pressure and hydrogen is supplied together, selectivity for C2+C6 hydrocarbons during the methane pyrolysis can be maximized.

Experimental Validation

Additional experiments were performed by setting the methane pyrolysis pressure below atmospheric pressure while supplying hydrogen. In order to sample the gaseous product discharged from a reactor equipped with a vacuum pump, volatile solids in the gas effluent flow were collected under mild conditions. As such, for the collected hydrocarbons, trace amounts of polycyclic aromatic hydrocarbons such as naphthalene, anthracene, and pyrene were also analyzed (data not shown). The gaseous product was then rapidly transferred to the analyzer over about 1 minute (FIG. 2).

Figure 6A:
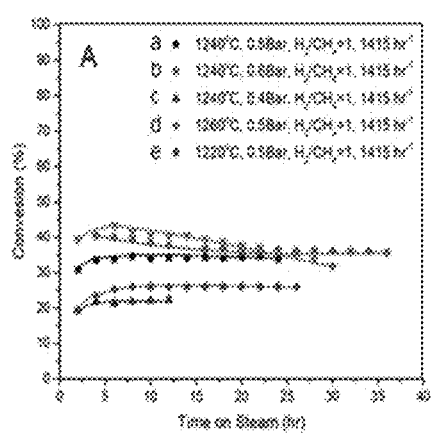
FIG. 6A is a graph showing the conversion of methane versus TOS (time on stream) under different pyrolysis conditions.
Figure 6B:
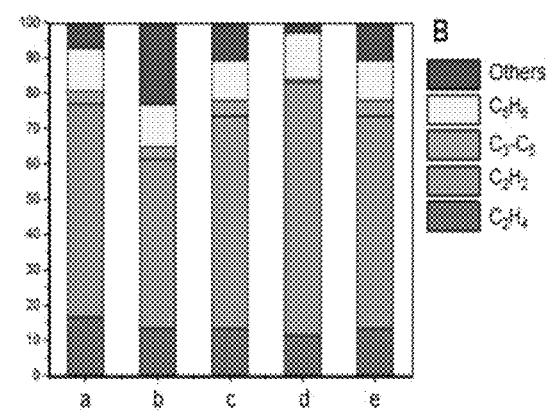
FIG. 6B is a graph showing the average selectivity of products under different pyrolysis conditions.

The results of the methane pyrolysis experiment are shown in FIGS. 6A and 6B. Operating conditions including a temperature of 1240° C., a $H_2/CH_4$ ratio of 1, a pressure of 0.5 bar, and a GHSV of 1415 $hr^{-1}$ were selected as the base experimental conditions for the methane pyrolysis. Under these conditions, the average conversion of methane was 34%, and the selectivity for heavy hydrocarbons to benzene was 93%. When the operating pressure was increased to 0.6 bar, the initial conversion increased to 41% and then gradually decreased to 36%, which can be seen as a problem related to heat transfer due to the formation of coke on the wall of the alumina tube reactor. On the other hand, when the reaction pressure started at 0.4 bar, the average conversion of methane was rapidly decreased to 21%, which was consistent with a simulation result showing that the methane conversion was sensitive to the reaction pressure as described above. When the temperature was raised under a fixed operating pressure, the increased initial conversion of 43% decreased to 32% after 30 hours. This result indicates that a reaction temperature suitable for stable hydrocarbon production in the methane pyrolysis should be selected. In addition, stable methane conversion of 26% and hydrocarbon selectivity of 95% were obtained under the mildest conditions of 1220° C. and 0.5 bar.

Figure 7:
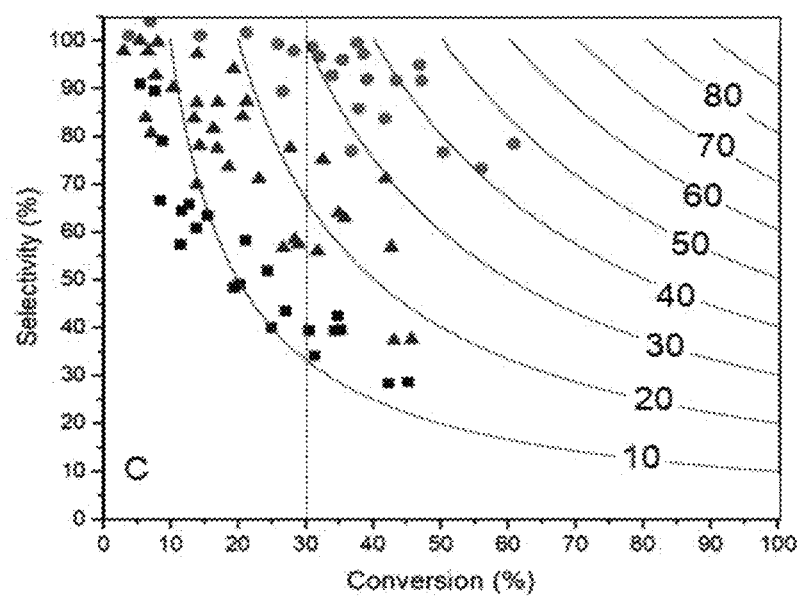
FIG. 7 is a graph showing the selectivity for $\leq C_6$ hydrocarbons versus conversion under different conditions (in which black squares represent $H_2/CH_4=0$ and atmospheric pressure conditions, blue triangles represent $H_2/CH_4=1$ and atmospheric pressure conditions, red circles represent $H_2/CH_4=1$ and sub-atmospheric pressure conditions, contour lines represent yield, and each point represents the average value in individual experiments)

Meanwhile, FIG. 7 shows experimental results plotting conversion versus selectivity for particular hydrocarbons. Similar to the simulation shown in FIG. 7, the experimental results were classified into three zones depending on whether hydrogen was supplied and on the reaction pressure. In this experiment, in order to achieve the target methane conversion, the temperature was adjusted within the range of 1000 to 1260° C.

According to the experimental results, high selectivity for hydrocarbons (C2+C6) was obtained at a methane conversion of less than 10% (the black squares in FIG. 7). However, when the methane conversion increased to about 40%, hydrocarbon selectivity was decreased sharply to about 30%, mainly due to the formation of polycyclic aromatic hydrocarbons and/or coke. When hydrogen was supplied thereto, the selectivity achievable at a methane conversion of 40% was about 80% (the blue triangles in FIG. 7). This is a result of the improved C2 selectivity, and indicates that hydrogen has a significant effect on suppressing the formation of polycyclic aromatic hydrocarbons. Moreover, when methane pyrolysis was carried out below atmospheric pressure, selectivity was increased. For example, the selectivity for hydrocarbons at a methane conversion of 50% was about 90% at an operating pressure of 0.3 to 0.5 bar. Based on the experimental results, the highest hydrocarbon yield was observed when the average conversion of methane was 36.9% at 1275° C. and 0.3 bar. These experimental results suggest that the methane pyrolysis is promising for production of three main species, namely acetylene, hydrogen, and benzene, under conditions in which the formation of coke precursors such as polycyclic aromatic hydrocarbons is suppressed.

Evaluation of Performance of Hydrogenation Catalyst

An effluent gas having a unique chemical composition was produced through the methane pyrolysis described above, and the methane pyrolysis product, in which the methane conversion was maintained at 30% and C7 or higher hydrocarbons were removed, was introduced as a feedstock for the hydrogenation. Polycyclic aromatic hydrocarbons were removed from methane pyrolysis products and trace amounts of C3-C5 hydrocarbons were not considered, and the composition thereof is shown in Table 1 below.

TABLE 1

| Classification | Partial pressure in gas mixture (Bar) | | | | |
|---|---|---|---|---|---|
| Methane conversion (%) | $CH_4$ | $H_2$ | $C_2H_4$ | $C_2H_2$ | $C_6H_6$ |
| 10 | 0.435 | 0.544 | 0.004 | 0.017 | 0.000 |
| 20 | 0.377 | 0.585 | 0.005 | 0.032 | 0.001 |
| 30 | 0.322 | 0.625 | 0.006 | 0.045 | 0.002 |
| 40 | 0.268 | 0.664 | 0.006 | 0.058 | 0.003 |
| 50 | 0.217 | 0.701 | 0.006 | 0.070 | 0.005 |

As shown in Table 1, when the methane conversion was about 30%, respective concentrations of methane, hydrogen, and acetylene in the gas mixture introduced into the hydrogenation reactor were 32.2%, 62.5%, and 4.5%, which were higher than for the gas composition used with palladium catalysts in commercial acetylene converters over the past few decades. In consideration thereof, in the present Example, a catalyst in which each of PdCu, PdAu, and PdAg was supported on an alumina support was applied. For screening, a catalyst was prepared by controlling the metal composition in a simple manner through incipient wetness impregnation.

FIG. 8A shows the overall yield of acetylene and benzene obtained from a hybrid system of methane pyrolysis and hydrogenation using a PdCu catalyst. As shown in this drawing, during the hydrogenation, 99.5% of acetylene was converted into ethylene using the PdCu catalyst, and deactivation of the catalyst was not observed even after 65 hours. The yields of ethylene and C2+C6 in the hybrid system were 20% and 24%, respectively. Although the PdAg catalyst and the PdAu catalyst showed lower catalytic performance than the PdCu catalyst, the PdAg catalyst also exhibited relatively high selectivity (98%) at a methane conversion of about 60%, and is thus regarded as promising (FIG. 8B). When using the PdAu catalyst, a high acetylene conversion was obtained, but ethane was the main product, indicating that the usefulness thereof in the selective hydrogenation of a gas mixture containing high-concentration acetylene and hydrogen is limited. These results suggest that the hybrid system according to the present Example has great potential in the continuous production of value-added ethylene from methane.

Meanwhile, the weight ratio between Pd and Cu supported on the hydrogenation catalyst was adjusted as shown in Table 2 below.

TABLE 2

| Active metal | 0.2Pd (Comparative Example) | 0.2Pd1Cu (Example) | 0.2Pd2Cu (Example) | 0.2Pd3Cu (Example) | 1Cu (Comparative Example) |
|---|---|---|---|---|---|
| Pd (wt %) | 0.215 | 0.215 | 0.217 | 0.215 | — |
| Cu (wt %) | — | 0.819 | 1.676 | 2.248 | 1.336 |

TABLE 3

| Catalyst | Temp. (° C.) | Acetylene conversion (%) | Selectivity (%) $C_2H_6$ | Selectivity (%) $C_2H_4$ |
|---|---|---|---|---|
| 0.2Pd (Comparative Example) | 50 | 99.9 | 91.9 | 8.1 |
| 0.2Pd1Cu (Example) | 50 | 96.7 | 10.5 | 89.5 |
| 0.2Pd2Cu (Example) | 50 | 14.9 | 4.5 | 95.5 |
| 0.2Pd2Cu (Example) | 100 | 99.5 | 4.0 | 96.0 |
| 0.2Pd3Cu (Example) | 100 | 97.5 | 3.0 | 97.0 |
| 1Cu (Comparative Example) | 300 | 17 | 2.6 | 97.4 |

As shown in Tables 2 and 3, in the presence of 0.2Pd not containing Cu (Comparative Example), a high conversion was realized compared to when using 0.2Pd1Cu, 0.2Pd2Cu, and 0.2Pd3Cu, all of which contained Cu, but the selectivity for ethylene was low, and moreover, in the presence of 1 Cu not containing Pd (Comparative Example), acetylene hydrogenation capability was remarkably low. In the presence of the catalysts containing Pd and Cu according to Examples, it was confirmed that conversion was decreased but selectivity for ethylene was increased at the same temperature with an increase in Cu content. In particular, the tendency toward increased selectivity with an increase in Cu content from 1 wt % to 3 wt % indicates that Pd atoms are arranged on Cu nanoparticles having low acetylene hydrogenation performance in the catalyst to thus create an environment in which Pd atoms can selectively hydrogenate acetylene, thereby realizing selective hydrogenation of high-concentration acetylene.

As is apparent from the above description, a method of producing ethylene and hydrogen from a gas mixture according to an embodiment of the present disclosure is capable of producing ethylene at high yield by selectively hydrogenating acetylene in a gas mixture in the presence of a bimetallic supported catalyst, taking into consideration the composition of products containing acetylene at a relatively high concentration depending on reaction conditions during methane pyrolysis. Also, hydrogen can be recovered from the gas mixture, and thus can be utilized for applications that add value, and can be used as a hydrogen source necessary for the selective hydrogenation of acetylene, thereby obviating the need for separate supply of hydrogen from external sources. In addition, when methane and/or hydrogen among hydrogenation products are recycled to the upstream methane pyrolysis reaction, it is possible to increase the conversion of methane and suppress coke formation during the methane pyrolysis. In particular, selectivity for acetylene can be increased, making it possible to form a gas mixture having a composition in which acetylene accounts for most C2 hydrocarbons in methane pyrolysis products. As such, the method according to the present embodiment is particularly advantageous for commercialization, such as improvement in the overall efficiency of conversion of methane into value-added platform chemicals, etc., through a selective hydrogenation process alone or in combination with processes upstream and downstream thereof.

Simple modifications or variations of the present invention can be easily devised by those of ordinary skill in the art, and all such modifications or variations can be considered to be included in the scope of the present invention.

The invention claimed is:

1. A selective hydrogenation method, comprising the steps of:
   step a) providing a gas mixture containing 2 to 10 mol % of acetylene, 50 to 75 mol % of hydrogen, 18 48 mol % of methane, and a concentration of C2 hydrocarbon other than acetylene being less than 1 mol %;
   step b) forming a hydrogenation product having an increased ethylene concentration compared to the gas mixture by hydrogenating the gas mixture in presence of a hydrogenation catalyst in which a first metal ($M_1$) having hydrogenation activity and a second metal ($M_2$) having a function of inducing selective hydrogenation are loaded on a porous support; and
   step c) separating and recovering ethylene and hydrogen from the hydrogenation product,
   in which the first metal ($M_1$) is at least one selected from the group consisting of Pd, Pt, Rh, Ir, Ni, and Co, and the second metal ($M_2$) is at least one selected from the group consisting of Cu, Ag, Au, Zn, Ga, and Sn, and amounts of the first metal ($M_1$) and the second metal ($M_2$) in the hydrogenation catalyst are 0.15 to 2 wt % and 0.8 to 30 wt %, respectively, and satisfy Equation 1 below:

$$3 \leq \frac{W_{M2}}{W_{M1}} < 20 \qquad \text{[Equation 1]}$$

wherein $W_{M1}$ is a wt % of the first metal in the hydrogenation catalyst and $W_{M2}$ is a wt % of the second metal in the hydrogenation catalyst.

2. The method of claim 1, wherein the gas mixture provided in step a) is obtained by removing aromatics from a methane pyrolysis product.

3. The method of claim 1, wherein a source of the methane in the gas mixture is at least one selected from the group consisting of methane, natural gas, and biogas.

4. The method of claim 1, further comprising recycling methane and at least a portion of hydrogen in the hydrogenation product to a methane pyrolysis.

5. The method of claim 4, wherein a recycled $CH_4/H_2$ molar ratio ranges from 0.05 to 1.

6. The method of claim 1, wherein the gas mixture contains 3 to 10 mol % of acetylene, 52 to 75 mol % of hydrogen, and 18 to 45 mol % of methane.

7. The method of claim 1, wherein the gas mixture further contains at least one selected from the group consisting of C3 to C5 hydrocarbons, a concentration thereof being less than 1 mol %.

8. The method of claim 1, wherein step b) is performed without any external supply of hydrogen.

9. The method of claim 1, wherein the first metal ($M_1$) and the second metal ($M_2$) in the hydrogenation catalyst are palladium (Pd) and copper (Cu), respectively.

10. The method of claim 1, wherein the porous support in the hydrogenation catalyst is at least one selected from the group consisting of alumina, silica, carbon, zirconia, titania, ceria, and silicon carbide.

11. The method of claim 10, wherein the porous support has a specific surface area (BET) of at least 300 $m^2/g$, a pore volume of at least 0.5 $cm^3/g$, and an average pore size of 50 to 200 Å.

12. The method of claim 1, wherein the hydrogenation catalyst is prepared by a method comprising: preparing a precursor solid by spray impregnating a support with a solution of a composite precursor in which a precursor of the first metal $M_1$ and a precursor of the second metal $M_2$ are combined.

13. The method of claim 12, wherein the method further comprises reducing the precursor of the first metal ($M_1$) and the precursor of the second metal ($M_2$) in the precursor solid at a temperature of 200 to 400° C. in a reducing atmosphere.

14. The method of claim 13, wherein the reducing is performed in an atmosphere of hydrogen alone or in an atmosphere in which hydrogen is diluted with an inert gas.

15. The method of claim 1, wherein the hydrogenating in step b) is performed at a temperature ranging from room temperature to 250° C. under a pressure of 0.2 to 1 bar.

16. The method of claim 15, wherein step b) is performed in a continuous mode, in which a gas hourly space velocity is adjusted within a range of 1 to 15 $L/g_{cat} \cdot hr^{-1}$.

* * * * *